(12) United States Patent
Ohgishi

(10) Patent No.: US 12,127,885 B2
(45) Date of Patent: Oct. 29, 2024

(54) ULTRASOUND TRANSDUCER UNIT AND ULTRASOUND ENDOSCOPE

(71) Applicant: OLYMPUS CORPORATION, Tokyo (JP)

(72) Inventor: Kozue Ohgishi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 221 days.

(21) Appl. No.: 17/864,758

(22) Filed: Jul. 14, 2022

(65) Prior Publication Data

US 2022/0346754 A1    Nov. 3, 2022

Related U.S. Application Data

(63) Continuation of application No. PCT/JP2020/002191, filed on Jan. 22, 2020.

(51) Int. Cl.
*A61B 8/00* (2006.01)
*A61B 8/12* (2006.01)
*B06B 1/06* (2006.01)

(52) U.S. Cl.
CPC .............. *A61B 8/4494* (2013.01); *A61B 8/12* (2013.01); *A61B 8/4488* (2013.01); *B06B 1/0625* (2013.01); *B06B 2201/76* (2013.01)

(58) Field of Classification Search
CPC ................................. A61B 8/12; B06B 1/0625
See application file for complete search history.

(56) References Cited

U.S. PATENT DOCUMENTS

2006/0058676 A1\* 3/2006 Yagi .................... G01N 29/225
                                                              600/459
2007/0293762 A1   12/2007 Sawada et al.
(Continued)

FOREIGN PATENT DOCUMENTS

JP      2004-016725 A       1/2004
JP      2006-087463 A       4/2006
(Continued)

OTHER PUBLICATIONS

International Search Report dated Feb. 25, 2020 received in PCT/JP2020/002191.

*Primary Examiner* — Colin T. Sakamoto
*Assistant Examiner* — Tommy T Ly
(74) *Attorney, Agent, or Firm* — Scully, Scott, Murphy & Presser, P.C.

(57) ABSTRACT

An ultrasound transducer unit includes: a plurality of units each of which includes a piezoelectric element group, a wiring substrate that includes a plurality of wiring lines that are electrically connected to piezoelectric elements included in the piezoelectric element group, and a cable group that is electrically connected to the wiring lines included in the wiring substrate, that extends in a direction intersecting a longitudinal direction of each of the piezoelectric elements included in the piezoelectric element group, and that is formed into a helical shape; an outer surface support that supports, by using an outer surface of the outer surface support, the piezoelectric element group included in each of the plurality of units; and an inner surface support that supports an inner surface of the outer surface support. Cable groups included in the plurality of units constitute a multiple helical structure.

20 Claims, 15 Drawing Sheets

(56) References Cited

U.S. PATENT DOCUMENTS

| | | | | |
|---|---|---|---|---|
| 2009/0088631 A1* | 4/2009 | Dietz | ..................... | A61B 90/37 |
| | | | | 600/424 |
| 2010/0331763 A1* | 12/2010 | Wilson | ................... | A61B 17/22 |
| | | | | 29/428 |
| 2019/0069878 A1 | 3/2019 | Irie | | |
| 2019/0133558 A1* | 5/2019 | Morimoto | ................ | A61B 8/12 |
| 2022/0008039 A1* | 1/2022 | Iguchi | ................... | A61B 8/4494 |

FOREIGN PATENT DOCUMENTS

| | | | |
|---|---|---|---|
| JP | 2006-191959 A | 7/2006 | |
| JP | 2006-271493 A | 10/2006 | |
| JP | 2008-289910 A | 12/2008 | |
| JP | 2014-166255 A | 9/2014 | |
| WO | WO-2013154684 A1 * | 10/2013 | ............ A61B 5/042 |
| WO | 2017/199571 A1 | 11/2017 | |

\* cited by examiner

ULTRASOUND TRANSDUCER UNIT AND ULTRASOUND ENDOSCOPE

CROSS-REFERENCE TO RELATED APPLICATION

This application is a continuation of International Application No. PCT/JP2020/002191, filed on Jan. 22, 2020, the entire contents of which are incorporated herein by reference.

BACKGROUND

1. Technical Field

The present disclosure relates to an ultrasound transducer unit and an ultrasound endoscope.

2. Related Art

In the related art, there is a known ultrasound transducer unit that is included in an ultrasound endoscope used for ultrasound observation to observe an inside of a subject and that is assembled into an insertion portion that is to be inserted into the inside of the subject (for example, see Japanese Laid-open Patent Publication No. 2008-289910).

The ultrasound transducer unit described in Japanese Laid-open Patent Publication No. 2008-289910 includes a plurality of piezoelectric elements that are regularly arrayed, a flexible substrate that includes a plurality of wiring lines that are electrically connected to the respective piezoelectric elements, and a plurality of cables that are electrically connected to the respective wiring lines. In addition, with the technology disclosed in Japanese Laid-open Patent Publication No. 2008-289910, flexible substrates that are divided into a plurality of blocks are helically wound, so that bendability is enhanced.

SUMMARY

In some embodiments, an ultrasound transducer unit includes: a plurality of units each of which includes a piezoelectric element group in which a plurality of piezoelectric elements are arrayed so as to be uniformly aligned in a longitudinal direction of each of the piezoelectric elements, a wiring substrate that includes a plurality of wiring lines that are electrically connected to the respective piezoelectric elements included in the piezoelectric element group, and a cable group that is electrically connected to the wiring lines included in the wiring substrate, that extends in a direction intersecting the longitudinal direction of each of the piezoelectric elements included in the piezoelectric element group, and that is formed into a helical shape; an outer surface support that supports, by using an outer surface of the outer surface support, the piezoelectric element group included in each of the plurality of units; and an inner surface support that supports an inner surface of the outer surface support. Cable groups included in the plurality of units constitute a multiple helical structure.

In some embodiments, an ultrasound endoscope includes: the ultrasound transducer unit; and an insertion portion in which the ultrasound transducer unit is assembled, the insertion portion being configured to be inserted into a subject.

In some embodiments, an ultrasound transducer unit includes: a piezoelectric element group that is formed into a tubular shape and in which a plurality of piezoelectric elements are arrayed so as to be uniformly aligned in a longitudinal direction of each of the piezoelectric elements; a plurality of wiring substrates each of which includes a plurality of wiring lines that are electrically connected to the respective piezoelectric elements included in the piezoelectric element group; a plurality of cable groups that are electrically connected to the respective wiring lines included in the respective wiring substrates, that extend in a direction intersecting the longitudinal direction of each of the piezoelectric elements included in the piezoelectric element group, and that are formed into a helical shape; an outer surface support that supports, by using an outer surface of the outer surface support, the piezoelectric element group; and an inner surface support that supports an inner surface of the outer surface support. Each wiring substrate includes a connecting portion that connects the wiring lines to respective cables included in each of the cable groups, each of the wiring lines and each of the cables are disposed in parallel in the connecting portion, and the cable groups constitute a multiple helical structure.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
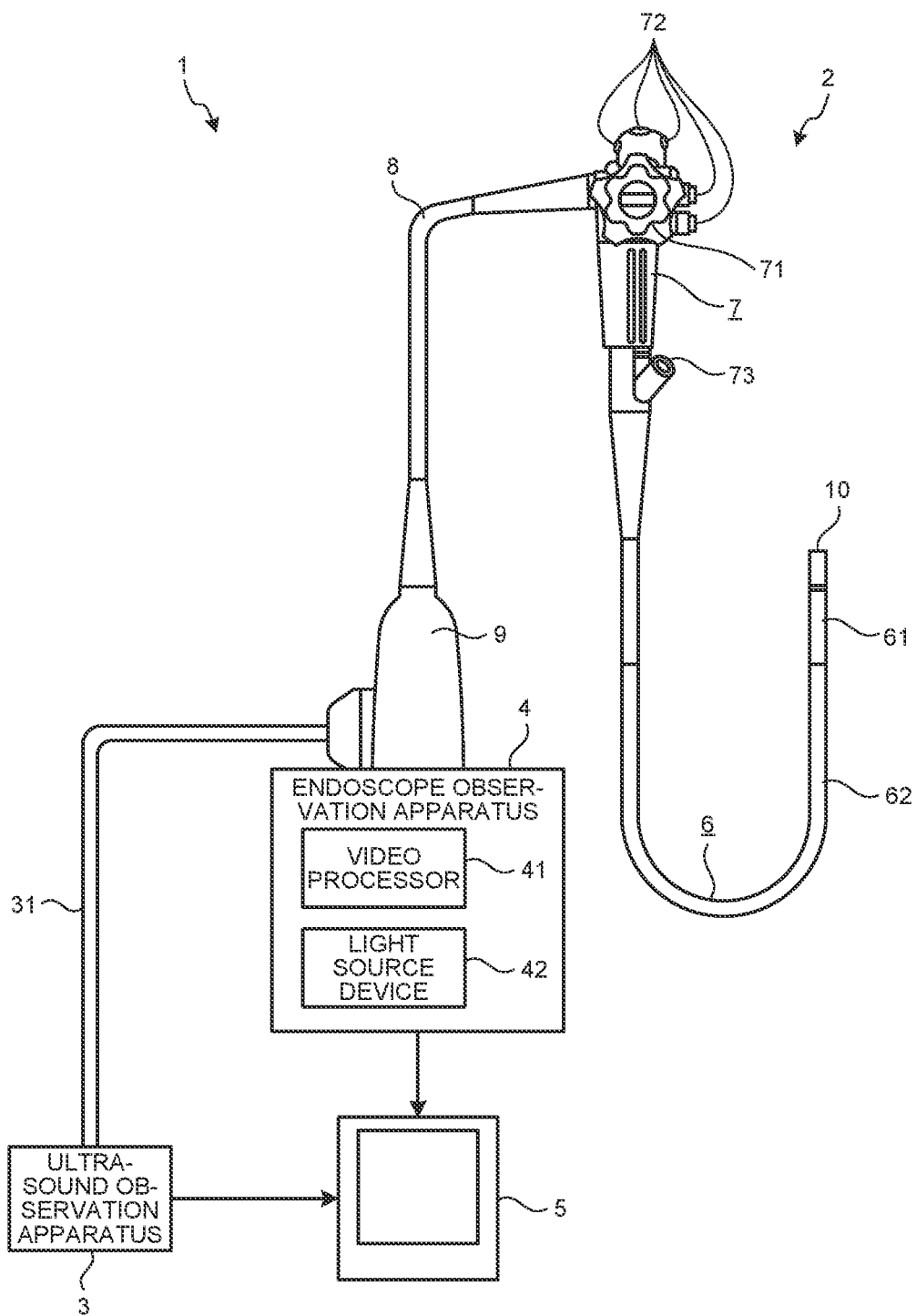
FIG. 1 is a diagram schematically illustrating an endoscope system according to the present embodiment.

Preferred embodiments of an ultrasound transducer unit and an ultrasound endoscope according to the disclosure will be explained with reference to accompanying drawings. Furthermore, the disclosure is not limited to the embodiments. In the embodiments described below, an ultrasound transducer unit and an ultrasound endoscope with a radial type are used an example; however, the disclosure can be applied to an ultrasound transducer unit and an ultrasound endoscope that are typically used.

Furthermore, in the descriptions of the drawings, components that are identical or corresponding to those in embodiments are assigned the same reference numerals. In addition, it is necessary to note that the drawings used for the descriptions below are only schematic illustrations the relationship of the size among the components, the ratios of the components, and so on may be different from those used in practice. Moreover, the drawings may include portions in which the relationship of the size among the components and the ratios of the components may sometimes differ between the drawings.

Embodiment

Schematic Configuration of Endoscope System

FIG. 1 is a diagram schematically illustrating an endoscope system according to the present embodiment. An endoscope system 1 is a system that makes an ultrasound diagnosis of an inside of a subject, such as a person, by using an ultrasound endoscope. The endoscope system 1 includes, as illustrated in FIG. 1, an ultrasound endoscope 2, an ultrasound observation apparatus 3, an endoscope observation apparatus 4, and a display device 5.

The ultrasound endoscope 2 includes a portion that is able to be inserted into a subject, and has a function for transmitting an ultrasound pulse (acoustic pulse) toward a body wall inside the subject, a function for receiving the ultrasound echoes reflected by the subject and outputting an echo signal, and a function for capturing images of the inside of the subject and outputting an image signal. Furthermore, a detailed configuration of the ultrasound endoscope 2 will be described later.

The ultrasound observation apparatus 3 is electrically connected to the ultrasound endoscope 2 via an ultrasound cable 31 (FIG. 1), outputs a pulse signal to the ultrasound endoscope 2 via the ultrasound cable 31, and inputs an echo signal from the ultrasound endoscope 2. Then, the ultrasound observation apparatus 3 generates an ultrasound image by performing a predetermined process on the echo signal.

An endoscope purpose connector 9 (FIG. 1) that will be described later and that is included in the ultrasound endoscope 2 is connected to the endoscope observation apparatus 4 so as to be freely attached to and removed from the endoscope observation apparatus 4. The endoscope observation apparatus 4 includes, as illustrated in FIG. 1, a video processor 41 and a light source device 42.

The video processor 41 inputs an image signal received from the ultrasound endoscope 2 via the endoscope purpose connector 9. Then, the video processor 41 generates an endoscope image by performing a predetermined process on the image signal.

The light source device 42 supplies, to the ultrasound endoscope 2 via the endoscope purpose connector 9, illumination light that illuminates the inside of the subject.

The display device 5 is constituted by using a liquid crystal or organic electro luminescence (EL), and displays an ultrasound image generated by the ultrasound observation apparatus 3, an endoscope image generated by the endoscope observation apparatus 4, or the like.

Configuration of Ultrasound Endoscope

In the following, a configuration of the ultrasound endoscope 2 will be described. The ultrasound endoscope 2 includes, as illustrated in FIG. 1, an insertion portion 6, an operating unit 7, a universal cord 8, and the endoscope purpose connector 9. Furthermore, a "distal end side" described below means a distal end side of the insertion portion 6 (the distal end side in an insertion direction in which the insertion portion 6 is inserted into the subject). Furthermore, a "proximal end side" described below means the side (the operating unit 7 side) that is away from the distal end of the insertion portion 6.

The insertion portion 6 is a portion that is inserted into the subject. The insertion portion 6 includes, as illustrated in FIG. 1, an ultrasound transducer unit 10 that transmits and receives ultrasound waves at the distal end portion, a bendable portion 61 that is coupled to the proximal end side of the ultrasound transducer unit 10 and that is freely bendable, and a flexible tube portion 62 that is coupled to the proximal end side of the bendable portion 61 and that has flexibility. Furthermore, a detailed configuration of the ultrasound transducer unit 10 that is assembled into the insertion portion 6 corresponding to the relevant part of the disclosure will be described later.

The operating unit 7 is a portion that is coupled to the proximal end side of the insertion portion 6 and that receives various operations from a doctor or the like. The operating unit 7 includes, as illustrated in FIG. 1, a bending knob 71 that allows the bendable portion 61 to perform bending operation, a plurality of operating members 72 used for performing various operations, and a treatment instrument insertion port 73 through which a treatment instrument is inserted.

The universal cord 8 is a code that extends from the operating unit 7, and in which a light guide that transmits the illumination light supplied from the light source device 42, a transducer cable that transmits the above described pulse signal or the above described echo signal, a signal cable that transmits the above described image signal, and the like are arranged.

The endoscope purpose connector 9 is provided at the end portion of the universal cord 8. In addition, the endoscope purpose connector 9 is a connector to which the ultrasound cable 31 is connected and that is connected to the video processor 41 and the light source device 42 as a result of the endoscope purpose connector 9 being inserted into the endoscope observation apparatus 4.

Configuration of Ultrasound Transducer Unit

Figure 2:
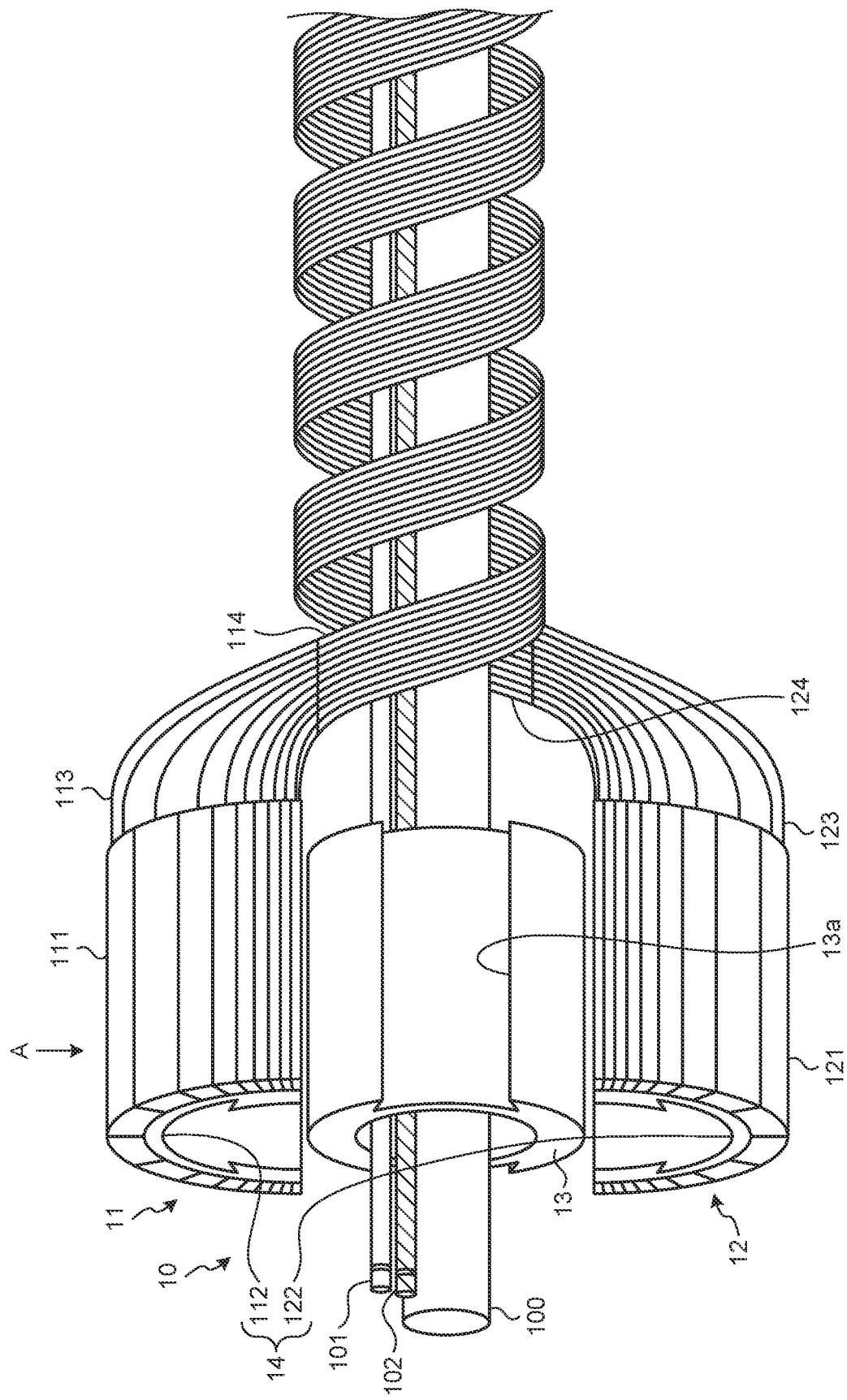
FIG. 2 is an exploded perspective view illustrating a configuration of an ultrasound transducer unit.

In the following, a configuration of the ultrasound transducer unit 10 will be described. FIG. 2 is an exploded perspective view illustrating the configuration of the ultrasound transducer unit. The ultrasound transducer unit 10 is, as illustrated in FIG. 2, an ultrasound transducer in which the distal end portion thereof is operated in an electronic radial scanning mode and that radially transmits ultrasound pulses. The ultrasound transducer unit 10 includes a first unit 11, a second unit 12, an inner surface support 13, and a support 14. A treatment instrument channel 100 that allows a treatment instrument that is inserted from the treatment instrument insertion port 73 provided in the operating unit 7 to protrude from the distal end of the insertion portion 6, an imaging unit 101 that captures an image of the inside of the subject, and an illumination unit 102 that irradiates the subject with illumination light received from the light source device 42 are inserted into the inner side of the ultrasound transducer unit 10.

The first unit 11 includes a first piezoelectric element group 111 in which a plurality of piezoelectric elements are arrayed so as to be uniformly aligned in a longitudinal direction, a first flexible substrate 113 that functions as a first wiring substrate and that includes a plurality of wiring lines that are electrically connected to the respective piezoelectric elements included in the first piezoelectric element group 111, and a first cable group 114 that is electrically connected to each of the wiring lines included in the first flexible substrate 113, that extends in a direction intersecting the longitudinal direction of each of the piezoelectric elements included in the first piezoelectric element group 111, and that is formed into a helical shape.

The second unit 12 includes a second piezoelectric element group 121 in which a plurality of piezoelectric elements are array so as to be uniformly aligned in a the longitudinal direction, a second flexible substrate 123 that functions as a second wiring substrate and that includes a plurality of wiring lines that are electrically connected to the respective piezoelectric elements included in the second piezoelectric element group 121, and a second cable group 124 that is electrically connected to each of the wiring lines included in the second flexible substrate 123, that extends in a direction intersecting the longitudinal direction of each of the piezoelectric elements included in the second piezoelectric element group 121, and that is formed into a helical shape together with the first cable group 114 in a translational manner.

The plurality of piezoelectric elements included in the first piezoelectric element group 111 and the second piezoelectric element group 121 are arrayed in a ring shape and constitute an ultrasound transducer with a radial type.

Each of piezoelectric elements included in the first piezoelectric element group 111 and the second piezoelectric element group 121 is formed by using a PMN-PT single crystal, a PMN-PZT single crystal, a PZN-PT single crystal, a PIN-PZN-PT single crystal, or a relaxer-based piezoelectric material. Furthermore, the PMN-PT single crystal is the abbreviated name for a solid solution of lead magnesium niobate and lead titanate. The PMN-PZT single crystal is the abbreviated name for a solid solution of lead magnesium niobate and lead zirconate titanate. The PZN-PT single crystal is the abbreviated name for a solid solution of lead zinc niobate and lead titanate. The PIN-PZN-PT single crystal is the abbreviated name for a solid solution of lead indium niobate, lead zinc niobate, and lead titanate. The relaxer-based piezoelectric material is a general name of a three-component system piezoelectric material made of adding lead-based complex perovskite that is a relaxer material to lead zirconate titanate (PZT) for the purpose of increasing a piezoelectric constant or a permittivity. Lead-based complex perovskite is denoted by $Pb(B1, B2)O_3$, where B1 is one of magnesium, zinc, indium and scandium, and B2 is one of niobium, tantalum, and tungsten. These materials have a superior piezoelectric effect. Accordingly, it is possible to lower the value of electrical impedance even if the size of the piezoelectric element is reduced.

Each of the first flexible substrate 113 and the second flexible substrate 123 is constituted by a plurality of wiring lines that are provided in association with the respective piezoelectric elements included in each of the first piezoelectric element group 111 and the second piezoelectric element group 121 and a substrate. The substrate is a substrate that is constituted from an insulating material made of polyimide or the like.

Figure 3:
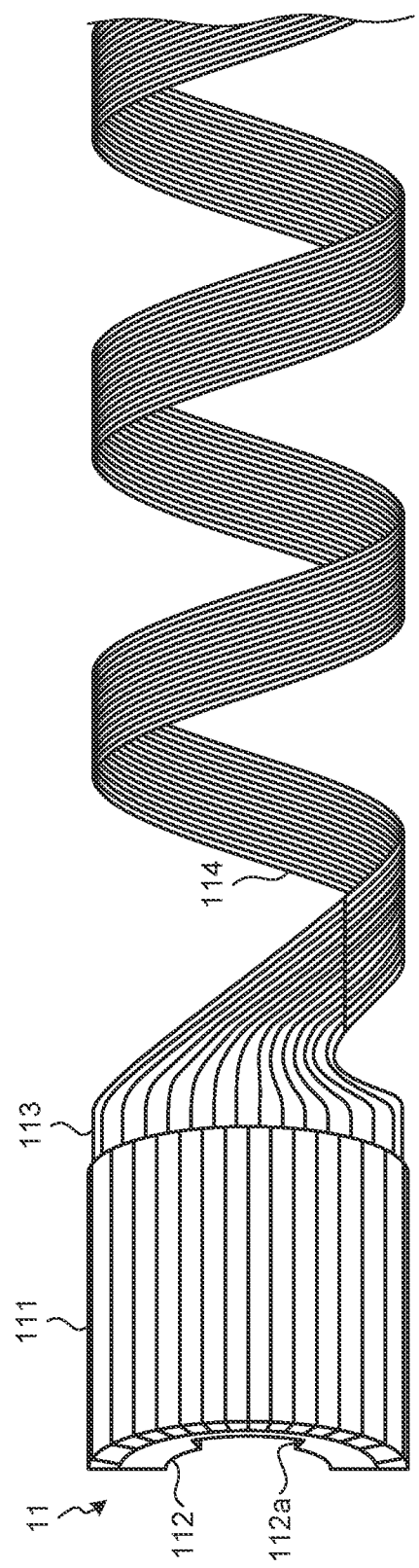
FIG. 3 is a diagram illustrating a first unit illustrated in FIG. 2 viewed from an arrow A.

FIG. 3 is a diagram illustrating the first unit illustrated in FIG. 2 viewed from an arrow A. The plurality of wiring lines included in the first flexible substrate 113 extend, on the first piezoelectric element group 111 side, along the longitudinal direction of each of the piezoelectric elements that are included in the first piezoelectric element group 111. In contrast, the plurality of wiring lines included in the first flexible substrate 113 extend, on the first cable group 114 side, in a direction that is parallel to the longitudinal direction of the first cable group 114 and that intersects the longitudinal direction of each of the piezoelectric elements that are included in the first piezoelectric element group 111. In addition, the first piezoelectric element group 111 extending along the longitudinal direction of the insertion portion 6 is electrically connected to the first cable group 114 that is formed into a helical shape. In other words, the plurality of wiring lines included in the first flexible substrate 113 are bent, so that a portion in which the first cable group 114 is bent is unneeded. As a result, a portion in which the first cable group 114 is bent does not need to be protected by a rigid material, so that it is possible to shorten the length of the rigid portion of the distal end disposed at the distal end of the insertion portion 6.

Similarly, the plurality of wiring lines included in the second flexible substrate 123 extend, on the second piezoelectric element group 121 side, along the longitudinal direction of each of the piezoelectric elements that are included in the second piezoelectric element group 121. In contrast, the plurality of wiring lines included in the second flexible substrate 123 extend, on the second cable group 124 side, in a direction that is parallel to the longitudinal direction of the second cable group 124 and that intersects the longitudinal direction of each of the piezoelectric elements that are included in the second piezoelectric element group 121. In addition, the second piezoelectric element group 121 extending along the longitudinal direction of the insertion portion 6 is electrically connected to the second cable group 124 that is formed into a helical shape. In other words, the plurality of wiring lines included in the second flexible substrate 123 are bent, so that a portion in which the second cable group 124 is bent is unneeded. As a result, a portion in which the second cable group 124 is bent does not need to be protected by a rigid material, so that it is possible to shorten the length of the rigid portion of the distal end disposed at the distal end of the insertion portion 6.

The inner surface support 13 is formed into a cylindrical shape and supports the inner surface of the support 14.

The support 14 includes a first support 112 that supports the first piezoelectric element group 111 by using an outer surface of the first support 112 and a second support 122 that supports the second piezoelectric element group 121 by using an outer surface of the second support 122.

Each of the first support 112 and the second support 122 also has a function as a backing member that attenuates unneeded ultrasound vibrations generated by an operation of the piezoelectric elements included in each of the first piezoelectric element group 111 and the second piezoelectric element group 121. Each of the first support 112 and the second support 122 is formed by using a material having a large attenuation rate, such as an epoxy resin in which a filler made of alumina, zirconia, or the like is dispersed or rubber in which the above described filler is dispersed.

Figure 4:
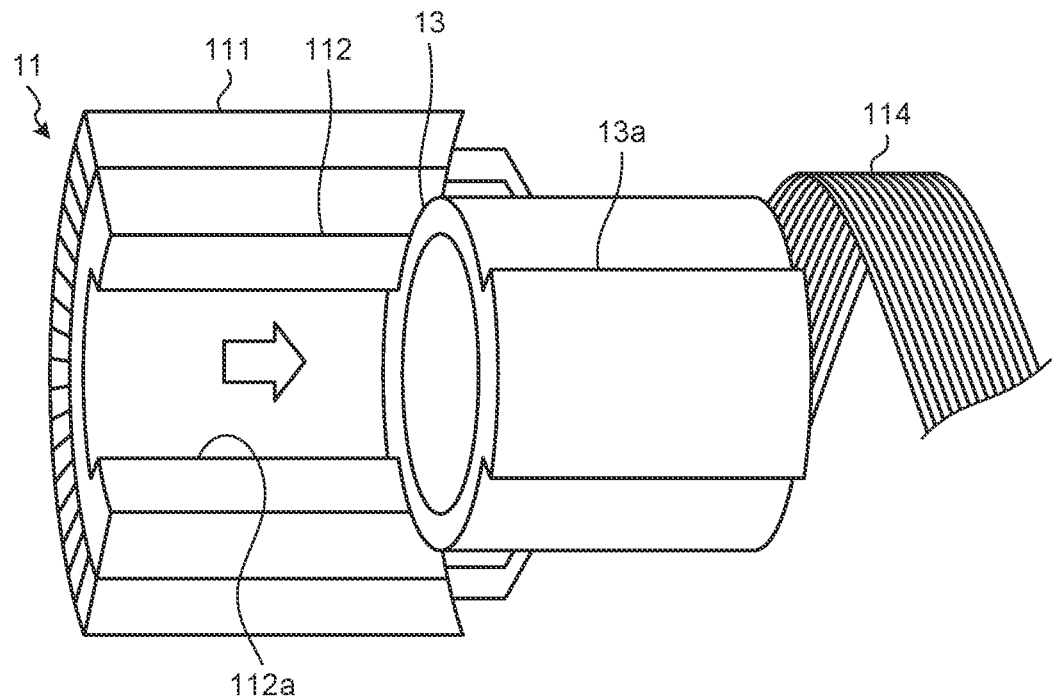
FIG. 4 is a diagram illustrating a state in which the first unit is attached to an inner surface support.

FIG. 4 is a diagram illustrating a state in which the first unit is attached to an inner surface support. As illustrated in FIG. 4, a dovetail groove 112a that is a recess portion is formed on the first support 112. A projection portion 13a that is fitted to the dovetail groove 112a is formed on the inner surface support 13. In addition, by assembling the first unit 11 from the distal end side of the inner surface support 13 such that the dovetail groove 112a is fitted to the projection portion 13a, the first unit 11 is formed in a state in which the first unit 11 is supported by the inner surface support 13.

Similarly, a dovetail groove 122a that is a recess portion is formed on the second support 122. The projection portion 13a that is fitted to the dovetail groove 122a is formed on the inner surface support 13. In addition, by assembling the second unit 12 from the distal end side of the inner surface support 13 such that the dovetail groove 122a is fitted to the projection portion 13a, the second unit 12 is formed in a state in which the second unit 12 is supported by the inner surface support 13. As a result of the dovetail groove 122a being fitted to the projection portion 13a, it is possible to perform position adjustment between the first unit 11 and the inner surface support 13. At this time, the position of the circumference of each of the piezoelectric elements included in the first piezoelectric element group 111 is also aligned with high accuracy.

However, the projection portion may be formed on each of the first support 112 and the second support 122, and the recess portion may be formed in the inner surface support 13.

According to the embodiment described above, the first cable group 114 and the second cable group 124 are formed into a helical shape in a translational manner, and the treatment instrument channel 100, the imaging unit 101, the illumination unit 102, and the like are inserted into a space located on the inner side of the first cable group 114 and the second cable group 124. As a result, it is possible to effectively use the space located on the inner side of the first cable group 114 and the second cable group 124, so that it is possible to reduce the diameter of the insertion portion 6 of the ultrasound endoscope 2.

Furthermore, according to the embodiment, in the event of a failure of the piezoelectric elements included in the first piezoelectric element group 111 or the second piezoelectric element group 121, it is possible to replace the failed piezoelectric elements included in the first unit 11 or the second unit 12. As a result, it is possible to reduce the cost at the time of repair of the piezoelectric element.

Furthermore, in the embodiment described above, a case has been described as an example in which the piezoelectric elements are divided into two unit (the first unit 11 and the second unit 12); however, the piezoelectric elements may be divided into three or more units. As the number of division is increased, the number of piezoelectric elements included in the unit that are replaced in the event of a failure of the piezoelectric elements is decreased, so that the effect of a reduction in cost at the time of repair of the piezoelectric elements is high.

Furthermore, in the embodiment described above, a case has been described as an example in which the piezoelectric elements are divided into two units (the first unit 11 and the second unit 12); however, the piezoelectric element need not be divided. For example, the piezoelectric element may be constituted as a single tubular unit, and furthermore, the flexible substrate and the cable group that are connected to the piezoelectric elements may be divided into two or more components. Also in this case, the divided two cable groups are formed into a helical shape in a translational manner with each other, and then, the treatment instrument channel 100, the imaging unit 101, the illumination unit 102, and the like are inserted into a space located in an inner side of the cable groups. As a result, it is possible to effectively use the space located in the inner side of the cable groups, so that it is possible to reduce the diameter of the insertion portion 6 of the ultrasound endoscope 2.

First Modification

Figure 5:
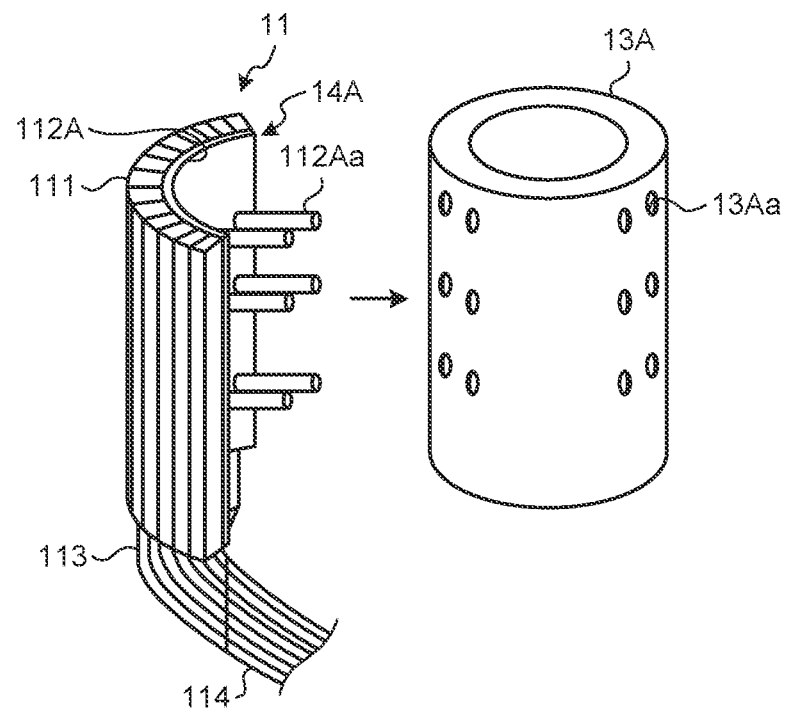
FIG. 5 is a diagram illustrating a relevant part of an ultrasound transducer unit according to a first modification of the embodiment.

FIG. 5 is a diagram illustrating a relevant part of an ultrasound transducer unit according to a first modification of the embodiment. As illustrated in FIG. 5, pins 112Aa each having a cylindrical shape are formed on a first support 112A included on a support 14A. Hole portions 13Aa each of which has a circular shape and is fitted to the associated pins 112Aa are formed on an inner surface support 13A. As in the first modification, each of the first unit and the second unit, and the inner surface support are not limited to the projection portion and the recess portion, but may be fitted by using the pins and the hole portions. In addition, each of the first unit and the second unit and the inner surface support may be fixed by an adhesive or the like.

Second Modification

Figure 6:
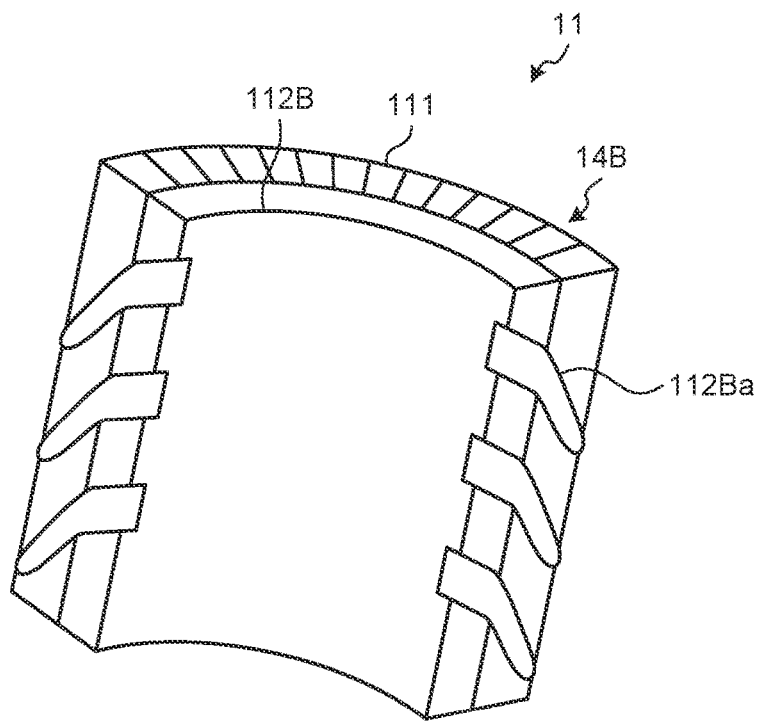
FIG. 6 is a diagram illustrating a relevant part of an ultrasound transducer unit according to a second modification of the embodiment.

FIG. 6 is a diagram illustrating a relevant part of an ultrasound transducer unit according to a second modification of the embodiment. As illustrated in FIG. 6, pins 112Ba each having a hook shape are formed on a first support 112B included in a support 14B. Hole portions that are fitted to the pins 112Ba are formed in the inner surface support. As in the second modification, the shape of each of the pins and the hole portions is not particularly limited.

Third Modification

Figure 7:
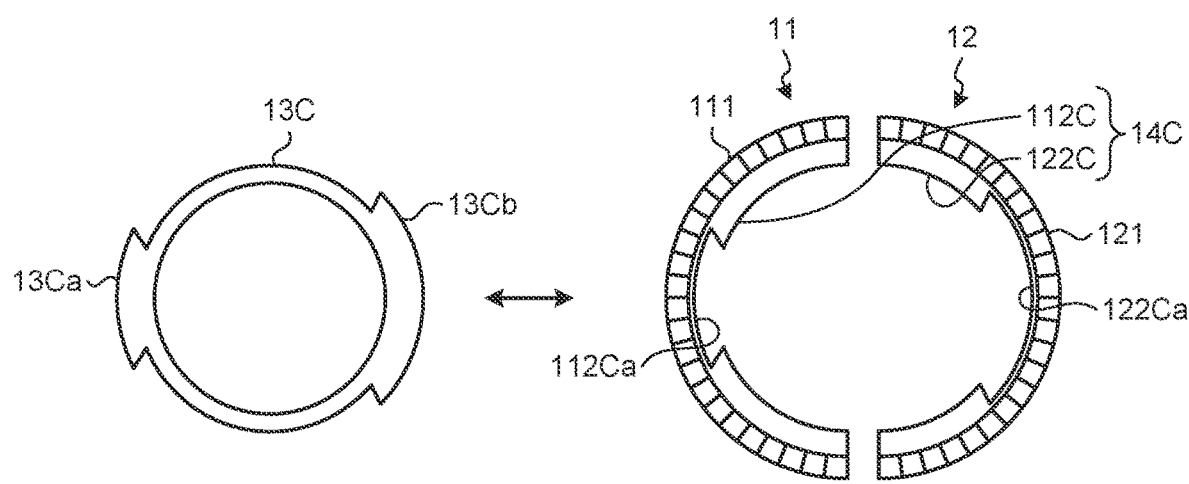
FIG. 7 is a diagram illustrating a relevant part of an ultrasound transducer unit according to a third modification of the embodiment.

FIG. 7 is a diagram illustrating a relevant part of an ultrasound transducer unit according to a third modification of the embodiment. As illustrated in FIG. 7, a dovetail groove 112Ca is formed in a first support 112C included in a support 14C. A dovetail groove 122Ca having a width that is wider than that of the dovetail groove 112Ca is formed in a second support 122C included in the support 14C. A projection portion 13Ca that is fitted to the dovetail groove 112Ca and a projection portion 13Cb that is fitted to the dovetail groove 122Ca are formed on an inner surface support 13C.

Each of the dovetail groove 112Ca and the dovetail groove 122Ca has a different width, it is possible to prevent confusion of installation positions when the first support 112C and the second support 122C are attached to the inner surface support 13C.

Fourth Modification

Figure 8:
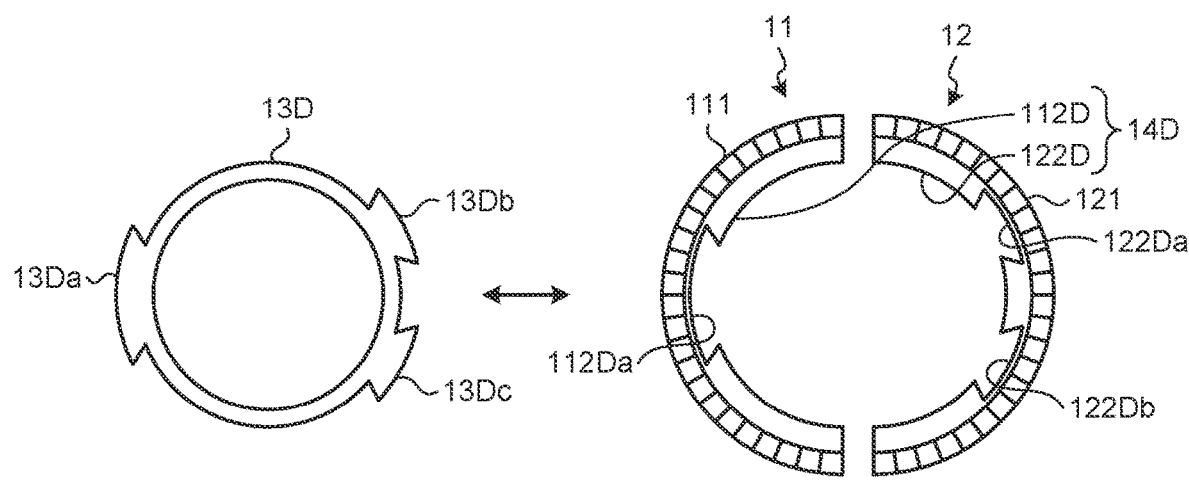
FIG. 8 is a diagram illustrating a relevant part of an ultrasound transducer unit according to fourth modification of the embodiment.

FIG. 8 is a diagram illustrating a relevant part of an ultrasound transducer unit according to fourth modification of the embodiment. As illustrated in FIG. 8, a dovetail groove 112Da is formed on a first support 112D included in a support 14D. A dovetail groove 122Da and a dovetail groove 122Db are formed on a second support 122D included in the support 14D. A projection portion 13Da that is fit to the dovetail groove 112Da, a projection portion 13Db that is fit to the dovetail groove 122Da, and a projection portion 13Dc that is fit to the dovetail groove 122Db are formed on an inner surface support 13D.

The number of dovetail grooves provided on the first support 112D is different from that provided on the second support 122D, so that it is possible to prevent confusion of installation positions when the first support 112D and the second support 122D are attached to the inner surface support 13D.

Fifth Modification

Figure 9:
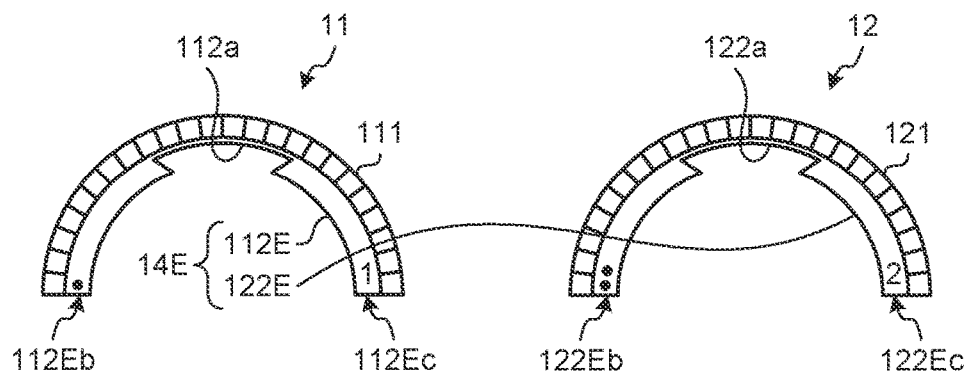
FIG. 9 is a diagram illustrating a relevant part of an ultrasound transducer unit according to a fifth modification of the embodiment.

FIG. 9 is a diagram illustrating a relevant part of an ultrasound transducer unit according to a fifth modification of the embodiment. As illustrated in FIG. 9, an indicator 112Eb denoted by a single point and an indicator 112Ec denoted by 1 that is a numerical character are provided on a first support 112E included in a support 14E. An indicator 122Eb denoted by two points and an indicator 122Ec denoted by 2 that is a numerical character are provided on a second support 122E included in the support 14E.

The first support 112E and the second support 122E are able to be identified by the indicator 112Eb, the indicator 112Ec, the indicator 122Eb, and the indicator 122Ec, so that it is possible to prevent confusion of installation positions when the first support 112E and the second support 122E are attached to the inner surface support. As in the fifth modification, the first support and the second support include the indicators that are able to be distinguished each other, so that it is possible to prevent confusion of installation positions.

Sixth Modification

Figure 10:
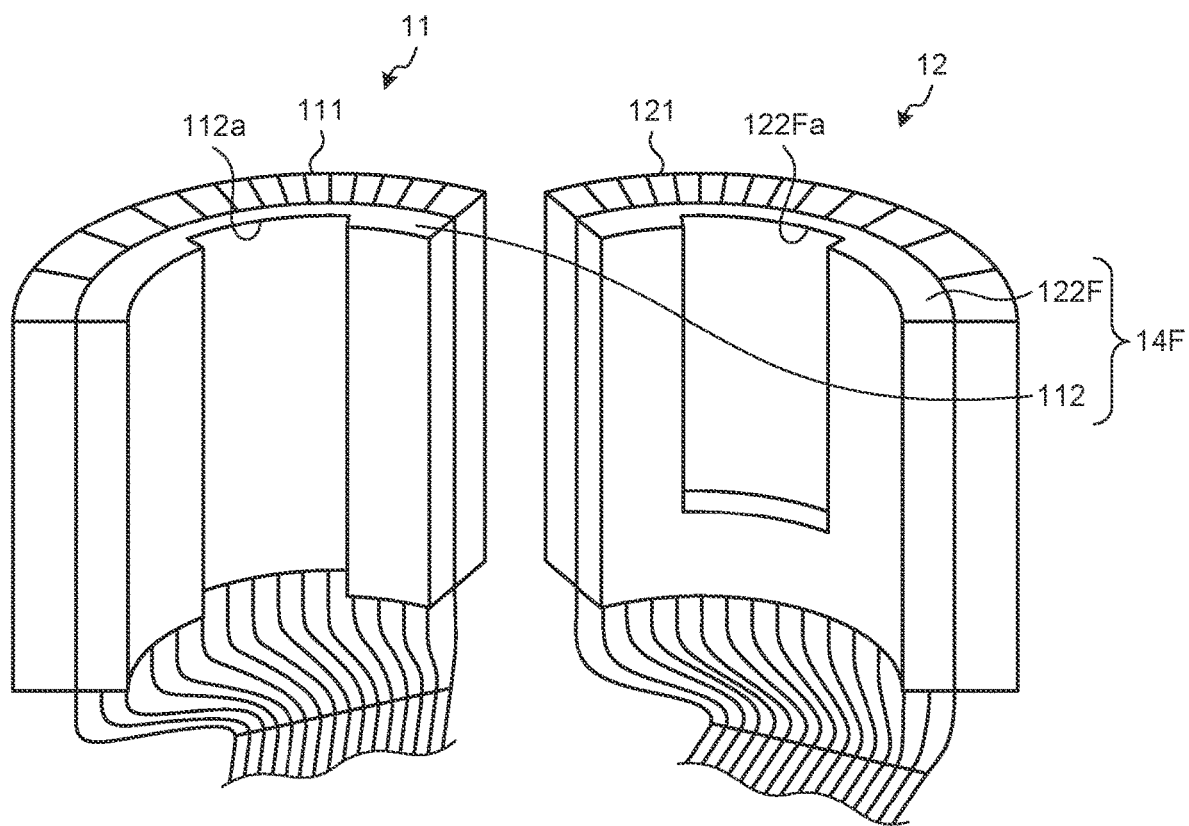
FIG. 10 is a diagram illustrating a relevant part of an ultrasound transducer unit according to a sixth modification of the embodiment.

FIG. 10 is a diagram illustrating a relevant part of an ultrasound transducer unit according to a sixth modification of the embodiment. As illustrated in FIG. 10, on a second support 122F included in a support 14F, a dovetail groove 122Fa that has a different shape from that of the dovetail groove 112a and in which the first cable group 114 side does not communicate with an end of the dovetail groove 122Fa is formed. On the inner surface support, a projection portion that has a shape fitted to the dovetail groove 122Fa is formed.

Each of the first support 112 and the second support 122F has a dovetail groove having a different shape, so that it is possible to prevent confusion of installation positions when the first support 112 and the second support 122F are attached to the inner surface support. As in the sixth modification, it may also be possible to prevent confusion of installation positions by allowing the first support and the second support to have different shapes.

Seventh Modification

Figure 11:
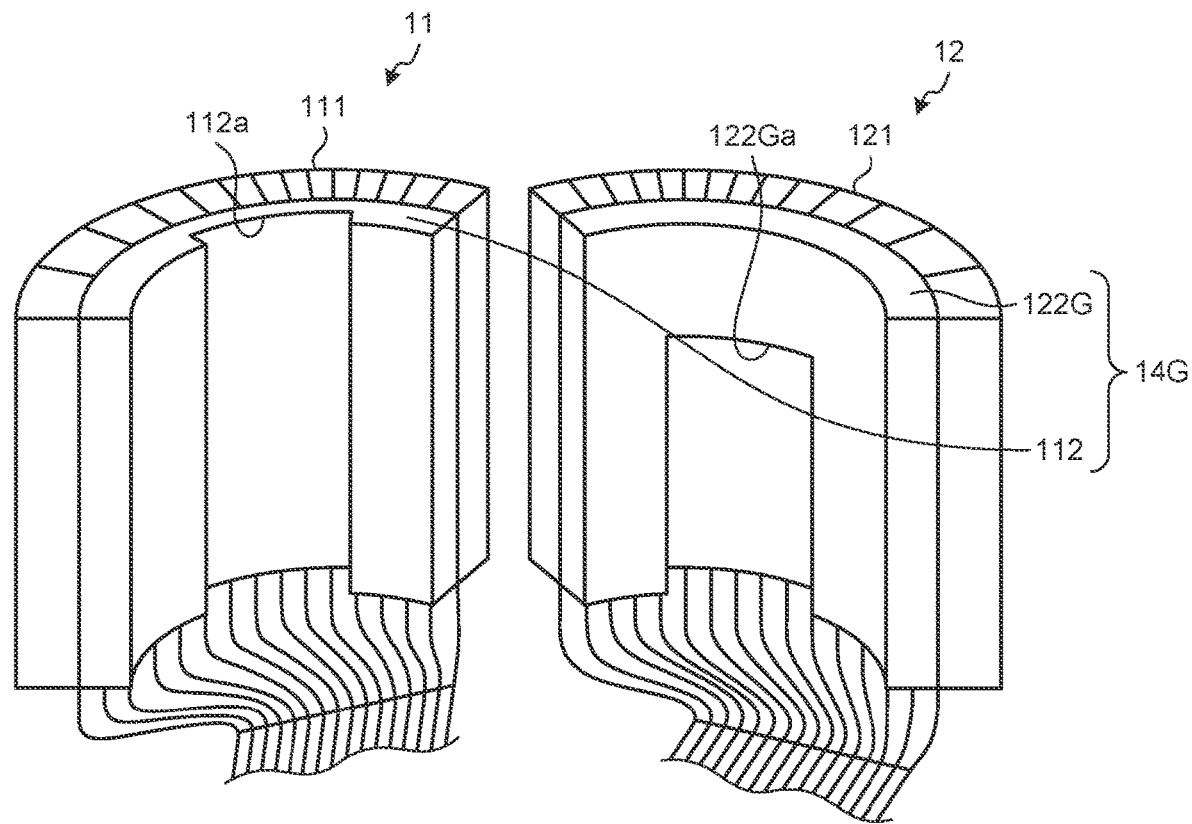
FIG. 11 is a diagram illustrating a relevant part of an ultrasound transducer unit according to a seventh modification of the embodiment.

FIG. 11 is a diagram illustrating a relevant part of an ultrasound transducer unit according to a seventh modification of the embodiment. As illustrated in FIG. 11, on a second support 122G included in a support 14G, a dovetail groove 122Ga that has a different shape from that of the dovetail groove 112a and in which the distal end side of the dovetail groove 122Ga does not communicate with the end portion of the second support 122G is formed. On the inner surface support, a projection portion that has a shape that is fitted to the dovetail groove 122Ga is formed.

Each of the first support 112 and the second support 122G has a dovetail groove having a different shape, so that it is possible to prevent confusion of installation positions when the first support 112 and the second support 122G are attached to the inner surface support. As in the seventh modification, the shape of each of the first support and the second support is not particularly limited as long as the shapes are different such that the first support and the second support are able to be identified.

Eighth Modification

Figure 12:
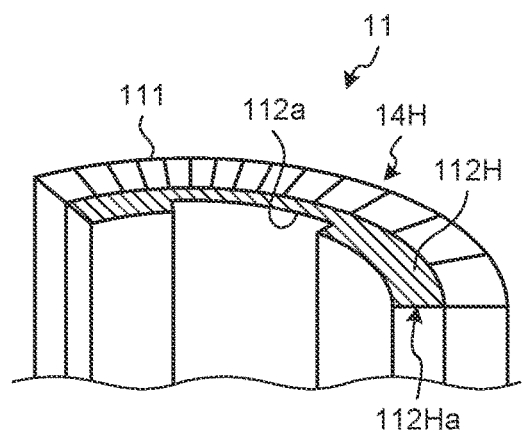
FIG. 12 is a diagram illustrating a relevant part of an ultrasound transducer unit according to an eighth modification of the embodiment.

FIG. 12 is a diagram illustrating a relevant part of an ultrasound transducer unit according to an eighth modification of the embodiment. On a first support 112H included in a support 14H, an end surface is colored as an indicator 112Ha. As in the eighth modification, a mode of the indicator is not particularly limited as long as the first support and the second support are able to be identified.

Ninth Modification

Figure 13:
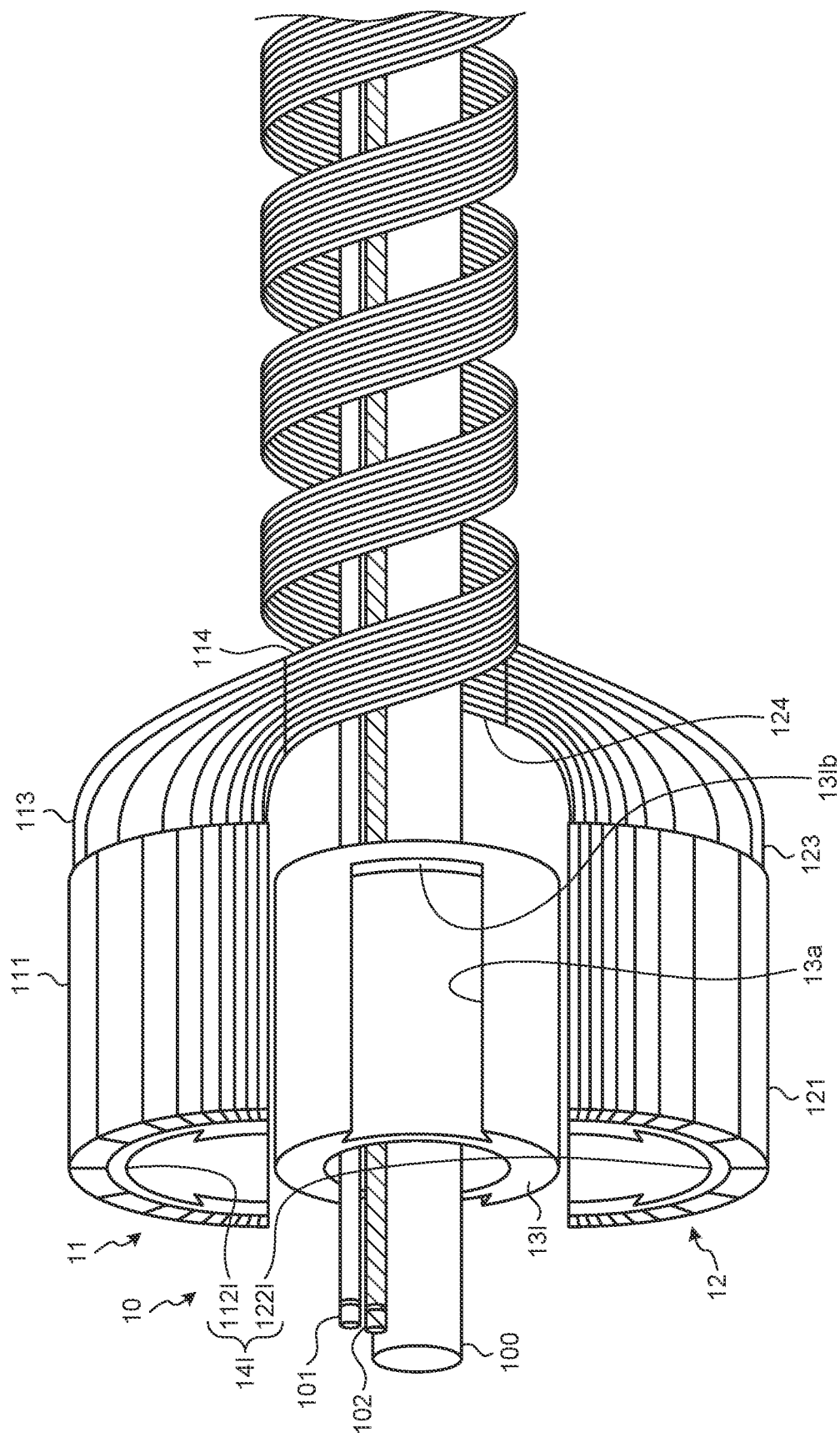
FIG. 13 is a diagram illustrating a relevant part of an ultrasound transducer unit according to a ninth modification of the embodiment.

FIG. 13 is a diagram illustrating a relevant part of an ultrasound transducer unit according to a ninth modification of the embodiment. As illustrated in FIG. 13, on the proximal end side of an inner surface support 13I, an abutting portion 13Ib that is a surface perpendicular to the longitudinal direction of the insertion portion 6 is formed. In addition, on a first support 112I and a second support 122I that are included in a support 14I, an abutting surface that abuts against the abutting portion 13Ib is formed. As a result, when the first support 112I and the second support 122I are assembled into the inner surface support 13I, position adjustment of the insertion portion 6 in the longitudinal direction with respect to positions between a position of the inner surface support 13I and positions of the first support 112I and the second support 122I is accurately performed, and thus, it is possible to prevent misalignment. In addition, the abutting portion 13Ib formed on the inner surface support 13I is abut against the abutting surface of each of the first support 112I and the second support 122I, so that it is possible to prevent an occurrence of misalignment of positions between the position of the inner surface support 13I and the positions of the first support 112I and the second support 122I due to a pulling force exerted on the first cable group 114 or the second cable group 124.

Tenth Modification

Figure 14:
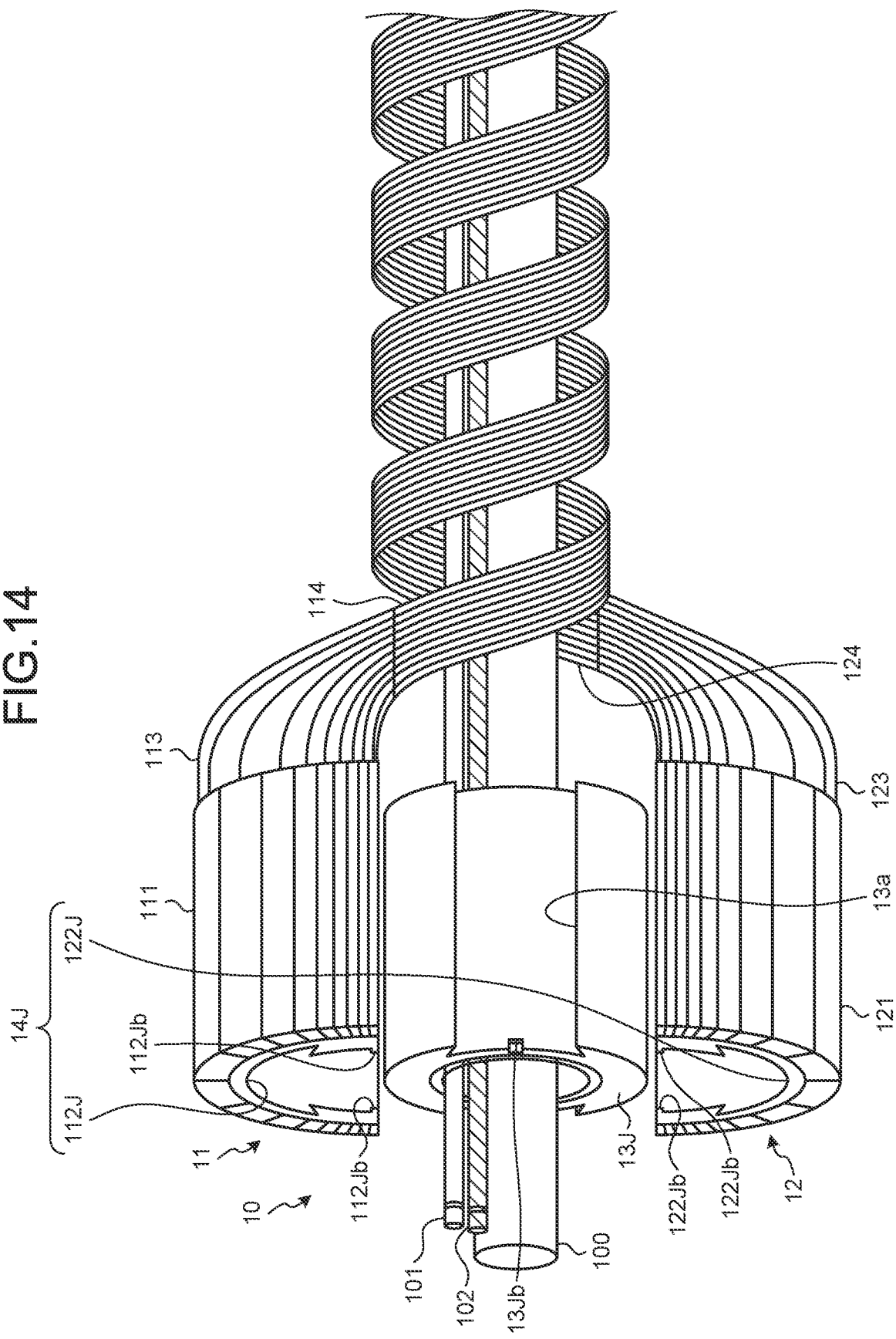
FIG. 14 is a diagram illustrating a relevant part of an ultrasound transducer unit according to a tenth modification of the embodiment.

FIG. 14 is a diagram illustrating a relevant part of an ultrasound transducer unit according to a tenth modification of the embodiment. As illustrated in FIG. 14, on the distal end of an inner surface support 13J, a recess portion 13Jb extending from the distal end of the an inner surface support 13J is formed. In addition, on a first support 112J and a second support 122J included in a support 14J, a projection portion 112Jb and a projection portion 122Jb that are fitted to the recess portion 13Jb are formed. As a result, when the first support 112J and the second support 122J are assembled into the inner surface support 13J, position adjustment of the longitudinal direction of the insertion portion 6 with respect to positions between a position of the inner surface support 13J and positions the first support 112J and the second support 122J and position adjustment of the circumference direction of the inner surface support 13J are accurately performed, and it is thus possible to prevent misalignment. Furthermore, the recess portion 13Jb included in the inner surface support 13J is fitted to the projection portion 112Jb and the projection portion 122Jb included in the first support 112J and the second support 122J, respectively, it is possible to prevent an occurrence of misalignment of positions between a position of the inner surface support 13J and positions of the first support 112J and the second support 122J due to a pulling force exerted on the first cable group 114 or the second cable group 124. In addition, when the inner surface support 13J is fixed to the first support 112J and a second support 122J by using an adhesive, the recess portion 13Jb has an effect of retaining the adhesive, so that it is possible to prevent the adhesive from being adhered to the treatment instrument channel 100, the imaging unit 101, the illumination unit 102, and the like that are inserted into the inside of the inner surface support 13J.

Detailed Configuration

Figure 15:
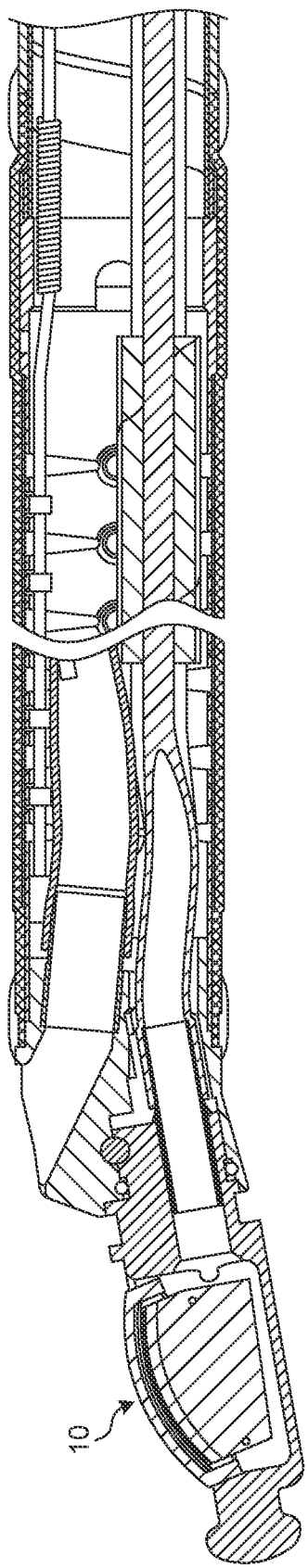
FIG. 15 is a diagram illustrating a modification of the ultrasound transducer unit.

FIG. 15 is a diagram illustrating a modification of the ultrasound transducer unit. As illustrated in FIG. 15, the ultrasound transducer unit 10 may be an ultrasound transducer with a convex type. The distal end portion of the ultrasound transducer unit 10 is bent to a rear surface side (on the opposite side of the side in which ultrasound waves are emitted).

Figure 16:
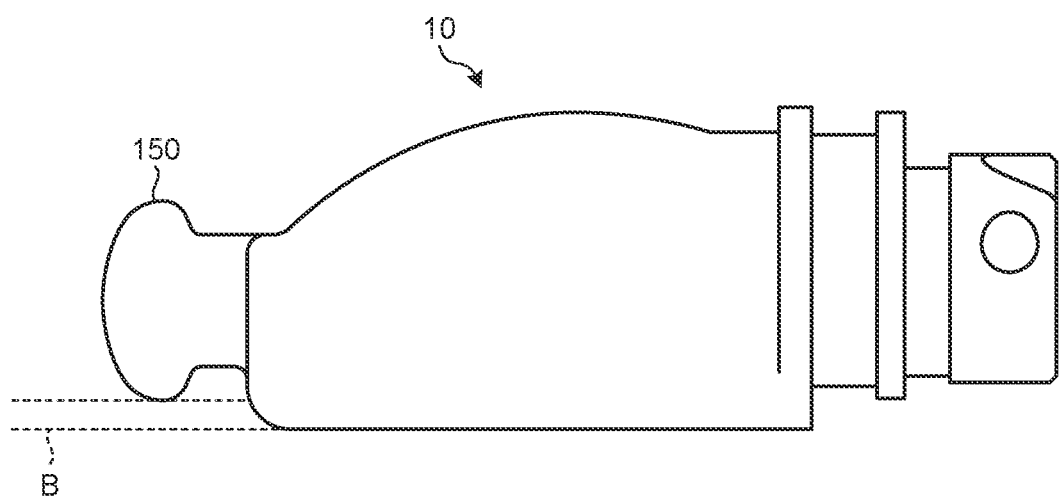
FIG. 16 is a magnified view of a distal end portion illustrated in FIG. 15.

FIG. 16 is a magnified view of a distal end portion illustrated in FIG. 15. As illustrated in FIG. 16, a protruding portion 150 that is located at the distal end of the ultrasound transducer unit 10 and that locks a balloon band is provided at a position further an inner side of a line B obtained when the rear surface of the ultrasound transducer unit 10 is projected toward the distal end side. As a result, mucosa or the like of the subject is prevented from being damaged by the protruding portion 150.

Figure 17:
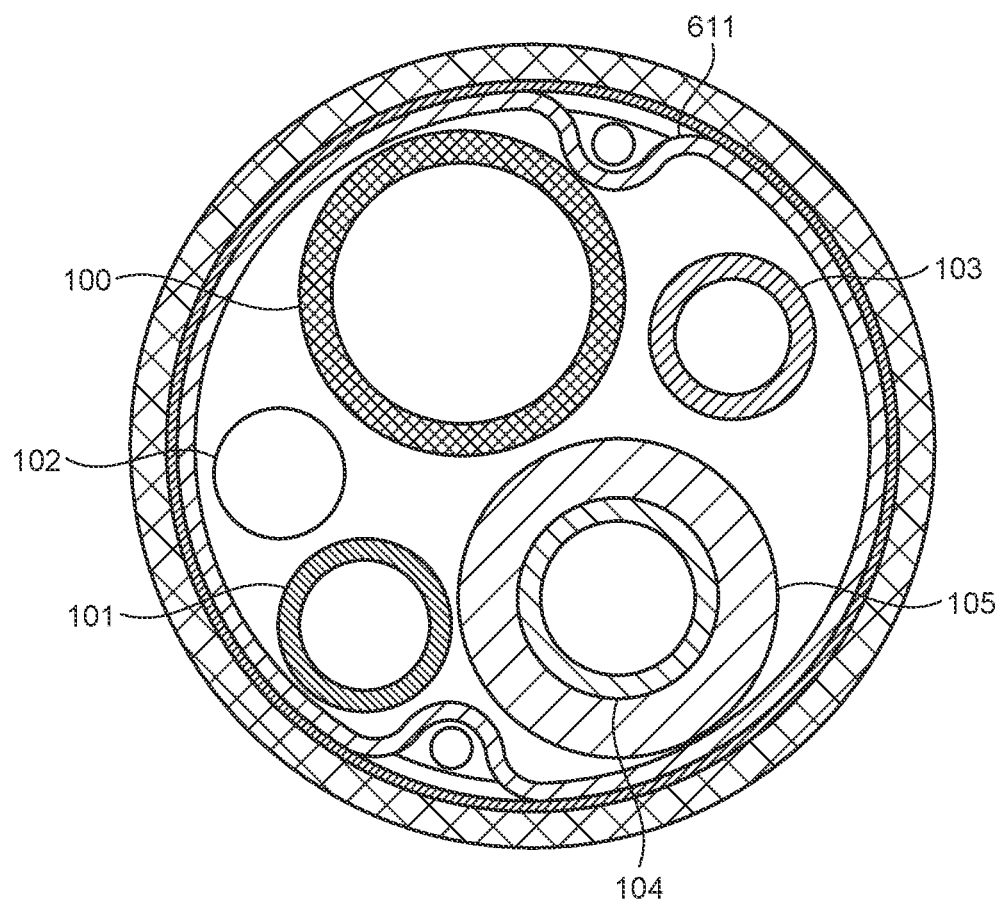
FIG. 17 is a cross-sectional view of a bendable portion.

FIG. 17 is a cross-sectional view of a bendable portion. At the bendable portion 61, on an inner side of a bending section 611, the treatment instrument channel 100, the imaging unit 101, the illumination unit 102, a balloon water supplying pipeline 103, and an ultrasound cable 104 are inserted. At this time, if a filling rate of the inner side of the bending section 611 is low, there may be a case in which these built-in members are twisted or buckled at the time of a bending operation. A spiral tube 105 is wound around the outer circumference of the ultrasound cable 104, so that the built-in members are prevented from being damaged by increasing the filling rata on the inner side of the bending section 611.

Figure 18:
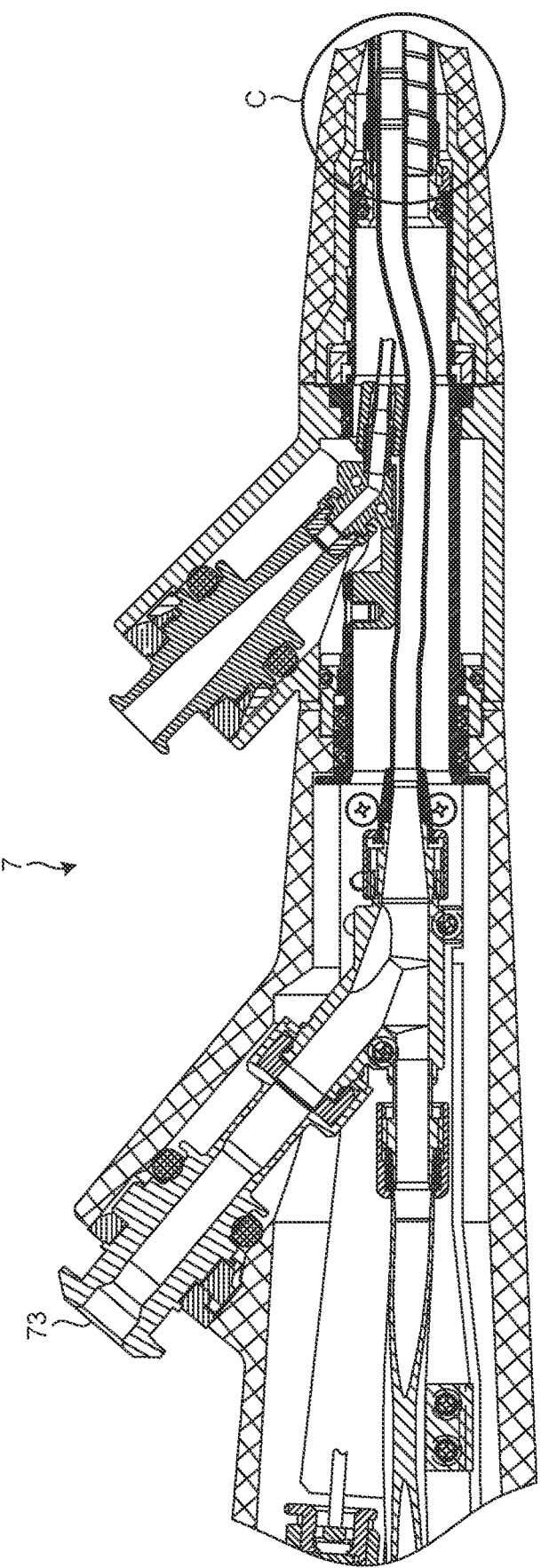
FIG. 18 is a cross-sectional view of an operating unit.
Figure 19:
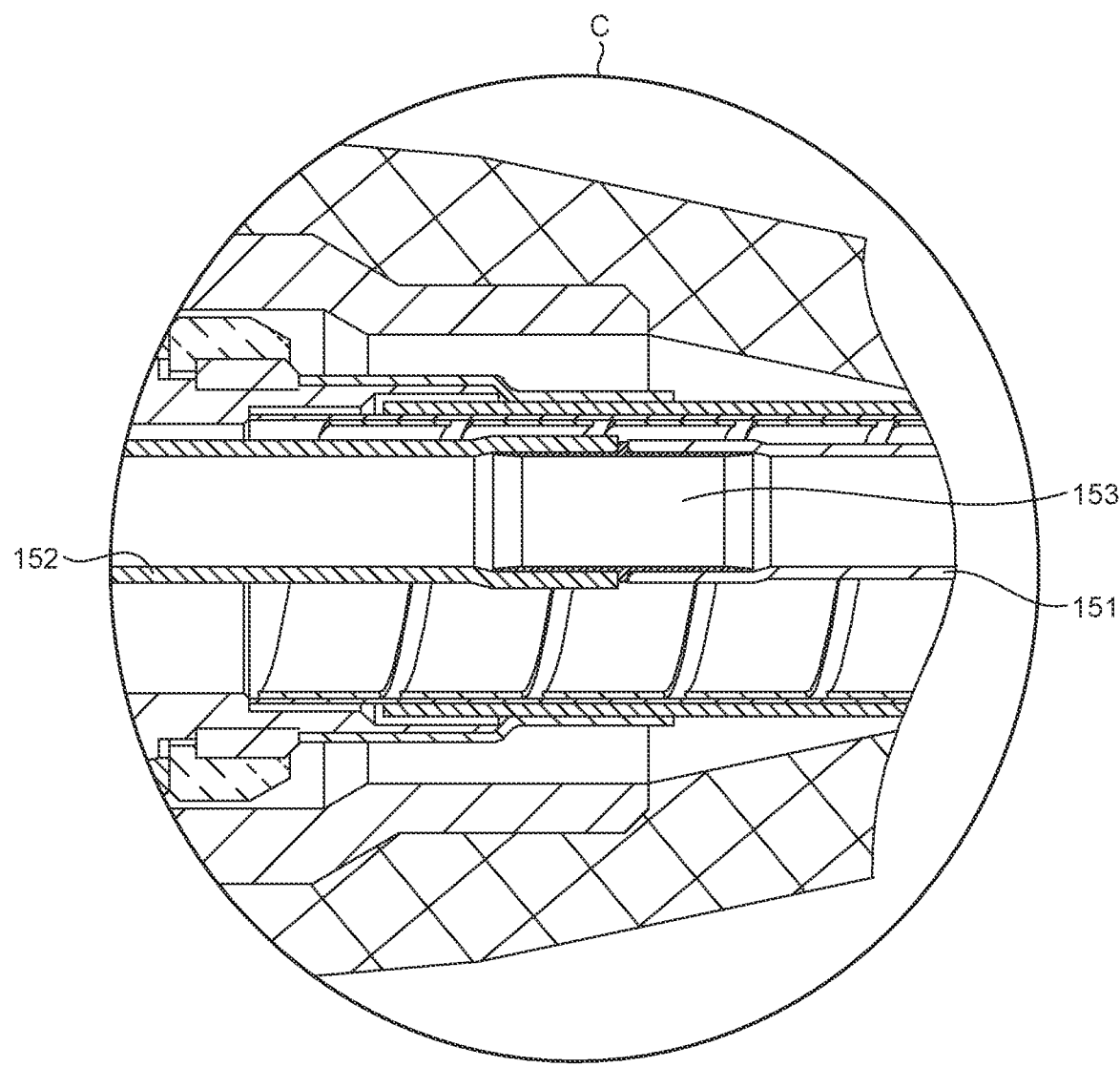
FIG. 19 is a magnified view of an area C illustrated in FIG. 18.

FIG. 18 is a cross-sectional view of an operating unit. FIG. 19 is a magnified view of an area C illustrated in FIG. 18. On the proximal end side of the operating unit 7, a tube 151 extending from the distal end of the insertion portion 6 is connected to a tube 152 extending from the treatment instrument insertion port 73 by using a pipe 153. As a result, the treatment instrument channel 100 is constituted such that a treatment instrument that is inserted from the treatment instrument insertion port 73 of the operating unit 7 is allowed to be projected from the distal end of the insertion portion 6.

Furthermore, the tube 151 is reinforced by providing a metal mesh; however, the metal mesh is not provided in the end portion of the proximal end side because the end portion is connected to the pipe 153. Accordingly, there may be a case in which the metal mesh comes loose when the end portion of the pipe 153 is inserted into a deeper position than the end portion of the metal mesh provided in the tube 151. In contrast, if a gap is present between the distal end of the pipe 153 and the end portion of the metal mesh of the tube 151, a subsidiary fracture may possibly occur from this gap. Position adjustment is accurately performed on the distal end of the pipe 153 and the end portion of the metal mesh of the tube 151, a portion in which the metal mesh is not provided in the tube 151 is formed in a transparent manner.

According to the disclosure, it is possible to implement an ultrasound transducer unit and an ultrasound endoscope that includes an insertion portion that is able to be reduced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer unit comprising:
a plurality of piezoelectric elements,
a first substrate,
a second substrate, the first substrate and the second substrate are connected to the plurality of piezoelectric elements,
a cable group comprising:
a first cable group connected to the first substrate, the first cable group having a first helical shape, and
a second cable group connected to the second substrate, the second cable group having a second helical shape, and
an imaging unit;
wherein the first cable group and second cable group are each helically wrapped around at least a proximal portion of the imaging unit.

2. The ultrasound transducer unit according to claim 1, wherein the first helical shape and the second helical shape have different helical phases with each other to not intersect with each other.

3. The ultrasound transducer unit according to claim 1, wherein the first helical, shape and the second helical shape each have a helical pitch greater than a total width of the cable group such that the first and second cable groups do not intersect with each other.

4. The ultrasound transducer unit according to claim 1, wherein the first and second helical shapes have a common central axis and the first and second cable groups are disposed so as to be axially symmetrical about the common central axis.

5. The ultrasound transducer unit according to claim 1, wherein
each of the first and second wiring substrates include a connector and wiring lines, the connector connects the wiring lines to the first and second cable groups, respectively.

6. The ultrasound transducer unit according to claim 5, wherein
each of the first substrate and the second substrate are flexible substrates, and
the wiring lines included in the first and second substrates extend, on a side of the cable group, in a direction intersecting a longitudinal direction of each of the plurality of piezoelectric elements.

7. The ultrasound transducer unit according to claim 1, further comprising:
an outer surface support, the plurality of piezoelectric elements located on the outer surface support;
an inner surface support, the outer surface support located on the inner surface support;
wherein the inner surface support having a cylindrical shape, and
the plurality of piezoelectric elements are arrayed in a ring shape.

8. The ultrasound transducer unit according to claim 7, wherein a pin and a hole are fitted with each other, the pin and the hole are located on the outer surface support and the inner surface support, respectively.

9. The ultrasound transducer unit according to claim 7, wherein
the outer surface support comprises first and second outer surface supports for supporting first and second portions of the plurality of piezoelectric elements, respectively, and
each of the first and second outer surface supports have indicators that are distinguishable from each other.

10. The ultrasound transducer unit according to claim 1, wherein a projection and a recess are fitted with each other, the projection and the recess are located on the inner surface support and the outer surface support, respectively.

11. The ultrasound transducer unit according to claim 10, wherein the recess is a dovetail groove.

12. The ultrasound transducer unit according to claim 1, wherein a first support and a second support support first and second portions of the plurality of piezoelectric elements, the first surface and the second surface have different shapes from each other.

13. An ultrasound endoscope comprising:
the ultrasound transducer unit according to claim 1; and
an insertion portion configured to be inserted into a subject, the ultrasound transducer being disposed at a distal end of the insertion portion.

14. The ultrasound transducer unit according to claim 1, wherein the plurality of piezoelectric elements radially surround a distal portion of the imaging unit.

15. The ultrasound transducer unit according to claim 1, wherein the first substrate and the second substrate are separable from each other such that the first substrate has first and second ends and the second substrate has third and fourth ends opposing the first and second ends.

16. The ultrasound transducer unit according to claim 1, further comprising:
an outer surface support that supports at least a portion of the plurality of piezoelectric elements, the outer surface support having one of a groove or a protrusion;
an inner surface support that supports an inner surface of the outer surface support, the inner surface support having an other of the groove or protrusion matingly engaged with the one of the groove or the protrusion.

17. The ultrasound transducer unit according to claim 16, wherein the outer surface support comprises:
a first outer surface support having a first inner surface and supporting a first portion of the plurality of piezoelectric elements, the first outer surface support having one of a first groove or a first protrusion; and
a second outer surface support having a second inner surface and supporting a second portion of the plurality of piezoelectric elements, the second outer surface support having one of a second groove or a second protrusion;
wherein the inner surface support supports each of the first inner surface and the second inner surface; and
the inner surface support having an other of the first groove and the first protrusion matingly engaged with the one of the first groove or the first protrusion and having an other of the second groove and the second protrusion matingly engaged with the one of the second groove or the second protrusion.

18. The ultrasound transducer unit according to claim 1, wherein the plurality of piezoelectric elements are arranged in a tubular shape.

19. An ultrasound transducer unit comprising:
a plurality of piezoelectric elements located on an outer surface,
the outer surface including a projection,
an inner surface having a cylindrical shape, the inner surface including a recess, the recess fitted with the projection,
a first substrate,
a second substrate, the first substrate and the second substrate are connected to the plurality of piezoelectric elements,
a cable group comprising:
a first cable group connected to the first substrate, the first cable group having a first helical shape, and
a second cable group connected to the second substrate, the second cable group having a second shape.

20. An ultrasound transducer unit comprising:
a plurality of piezoelectric elements,
a first substrate,
a second substrate, the first substrate and the second substrate are connected to the plurality of piezoelectric elements,
a cable group comprising:
a first cable group connected to the first substrate, the first cable group having a first helical shape, and
a second cable group connected to the second substrate, the second cable group having a second shape, wherein
each of the first and second wiring substrates include a connector and a plurality of wiring lines, the connector connects the plurality of wiring lines to the first and second cable groups, respectively and
the plurality of wiring lines included in the first and second wiring substrates extend, on a side of the cable group, in a direction intersecting a longitudinal direction of each of the plurality of piezoelectric elements.

\* \* \* \* \*